(12) United States Patent
Nishina et al.

(10) Patent No.: US 6,474,136 B1
(45) Date of Patent: Nov. 5, 2002

(54) METHOD AND APPARATUS FOR ANALYZING IMPURITIES IN GASES

(75) Inventors: Akira Nishina, Tokyo (JP); Makoto Tanaka, Tokyo (JP); Tetsuya Satou, Tokyo (JP)

(73) Assignee: Nippon Sanso Corporation, Tokyo (JP)

( * ) Notice: Subject to any disclaimer, the term of this patent is extended or adjusted under 35 U.S.C. 154(b) by 0 days.

(21) Appl. No.: 09/698,732

(22) Filed: Oct. 27, 2000

(30) Foreign Application Priority Data

Oct. 28, 1999 (JP) .......................... 11-306302

(51) Int. Cl.[7] .................. G01N 30/04; B01D 53/02
(52) U.S. Cl. ....................... 73/23.42; 96/102
(58) Field of Search .................. 73/23.35, 23.42, 73/23.37, 23.4, 24.02, 25.03; 96/102; 436/39

(56) References Cited

U.S. PATENT DOCUMENTS

| | | | |
|---|---|---|---|
| 3,753,656 A | * 8/1973 | Matson et al. ............... | 436/39 |
| 3,841,059 A | * 10/1974 | McCabe ...................... | 96/102 |
| 4,067,227 A | * 1/1978 | Johns et al. ................ | 73/23.35 |
| 4,713,362 A | * 12/1987 | Maroulis et al. ............ | 502/85 |
| 4,883,504 A | * 11/1989 | Gerstel ...................... | 95/8 |
| 5,611,846 A | * 3/1997 | Overton et al. ............. | 96/102 |
| 5,612,489 A | * 3/1997 | Ragsdale et al. ........... | 73/23.35 |
| 5,983,703 A | * 11/1999 | Wylie et al. ............... | 73/23.42 |
| 2001/0003290 A1 | * 6/2001 | Xu et al. .................... | 137/885 |

FOREIGN PATENT DOCUMENTS

| | | | |
|---|---|---|---|
| JP | 01072057 A | * 3/1989 | .......... G01N/30/72 |
| JP | 4001229964 | * 9/1989 | .......... G01N/30/30 |
| JP | 10300738 A | * 11/1998 | .......... G01N/30/44 |
| JP | 11153586 A | * 6/1999 | .......... G01N/30/26 |
| JP | 0200013130 | * 5/2000 | .......... G01N/30/46 |

OTHER PUBLICATIONS

Wadsworth, Handbook of Statistical Methods for Enigineers and Scientists, 1990, section 2.10.*
Wadsworth, Handbook of Statistical Methods for Engineers and Scientists, 1990, section 2.10.*

* cited by examiner

Primary Examiner—Daniel S. Larkin
Assistant Examiner—Jay L. Politzer
(74) Attorney, Agent, or Firm—Merchant & Gould P.C.

(57) ABSTRACT

There are provided a method and an apparatus capable of accurately analyzing impurity component having high adsorptivity or reactivity in a short time. Prior to starting measurement, predetermined amount of sample gas is introduced into analyzing system in plural times with predetermined time interval and then, analysis of impurities is started.

2 Claims, 3 Drawing Sheets

US 6,474,136 B1

METHOD AND APPARATUS FOR ANALYZING IMPURITIES IN GASES

BACKGROUND OF THE INVENTION

1. Field of the Invention

The present invention relates to a method and an apparatus for analyzing impurities in gases, and particularly to a method and an apparatus for analyzing trace impurities contained in gases having high adsorptivity or reactivity such as oxygen, silane, diborane, phosphine, arsine or the like.

2. Description of the Prior Art

There have been conventionally carried out a method where a gas chromatograph provided with a column for separating impurities in sample gases and a mass spectrometer which is a detector carrying out analysis of the impurity components are combined such that the trace impurity components to be measured are separated in the gas chromatograph and then, the respective components are measured in the mass spectrometer. However, according to this method, when 10 ppb level of impurities contained in, for example, oxygen which is one of the gases having high adsorptivity or reactivity is analyzed, even though the sample gas is introduced several times, background impurities to be measured are not stabilized and at the same time peak height of the impurities is always varied for each introduction of the sample gas. Therefore, when impurities in oxygen are analyzed, it is necessary to carry out an operation of stabilizing background and peak of the impurities by introducing oxygen scores of times through an operating and sampling valve, every time before starting measurement. Furthermore, when columns are separately used according to the impurities to be measured, it is necessary to carry out the same operation for the respective columns which thereby requires much labor and time.

Furthermore, when an atmospheric pressure ionization spectrometer is used as a detector for the impurity component, since the impurities are measured with higher sensitivity, for example, from 1 ppb to sub ppb level, stability of the background or peak height of the impurities is much affected by the mass spectrometer which thereby requires a much longer time for obtaining stable measurement values.

More particularly, with reference to oxygen analysis, Japanese Laid Open Gazette Hei 9-236564 discloses a detection method where parts having adsorptivity or reactivity within an apparatus are made to be saturated with oxygen by introducing carrier gas containing a small amount of oxygen in advance and then, sample gas is introduced for detection of a small amount of oxygen therein. This is a method where oxygen as an impurity is detected by using only a gas chromatograph 10 and the ppm level of impurity oxygen is detected while several ppm of oxygen is always introduced into the carrier gas.

However, since a regular amount of oxygen is introduced into the carrier gas, in the case of an analyzing apparatus which combines a gas chromatograph with a mass spectrometer or an atmospheric pressure ionization spectrometer, a relatively high-concentration oxygen of several ppm is always present in the analyzing part of the mass spectrometer or the atmospheric pressure ionization spectrometer. Thus, a problem is that deterioration of the ion source of the mass spectrometer or the atmospheric pressure ionization spectrometer is expedited, and the charge of ions of impurities are transferred to the oxygen which is easily ionized to thereby make it difficult to detect impurities in the case of the atmospheric pressure ionization spectrometer, and therefore sensitivity is decreased.

Therefore, the object of the present invention is to provide a method and an apparatus for analyzing impurities in gases capable of shortening conditioning time, and which is capable of obtaining stable measurement values with superior reproducibility in a short time, even when the atmospheric pressure ionization spectrometer is used as a detector.

SUMMARY OF THE INVENTION

To accomplish the above-mentioned object, according to the present invention, there is provided a method for analyzing impurities in a sample gas in a spectrometer after separating said impurities from columns in a gas chromatograph, said method comprising the steps of: with said spectrometer operationally off, introducing a predetermined amount of said sample gas into the analyzing system plural times for a predetermined time interval and turning said spectrometer operationally on and starting analysis of said impurities.

Furthermore, according to the present invention, there is provided an apparatus for analyzing impurities in gas, comprising columns for separating said impurities in gas and a detector for analyzing said impurities separated from said columns, said apparatus comprising: sample gas introduction passages diverged in plural wherein said respective passages are respectively provided with said column and sampling valve for metering and supplying said sample gas into said column, and a switch valve for switching gas flowing out from any one of said columns into a passage for supplying said gas into said detector via analyzing passage, and switching gas flowing out from the other of said columns into a passage for exhausting said gas outside of the analyzing system via an exhaust passage wherein said switch valves are provided downstream of said columns.

BRIEF DESCRIPTION OF THE INVENTION

DETAILED DESCRIPTION OF PREFERRED EMBODIMENTS

Figure 1:
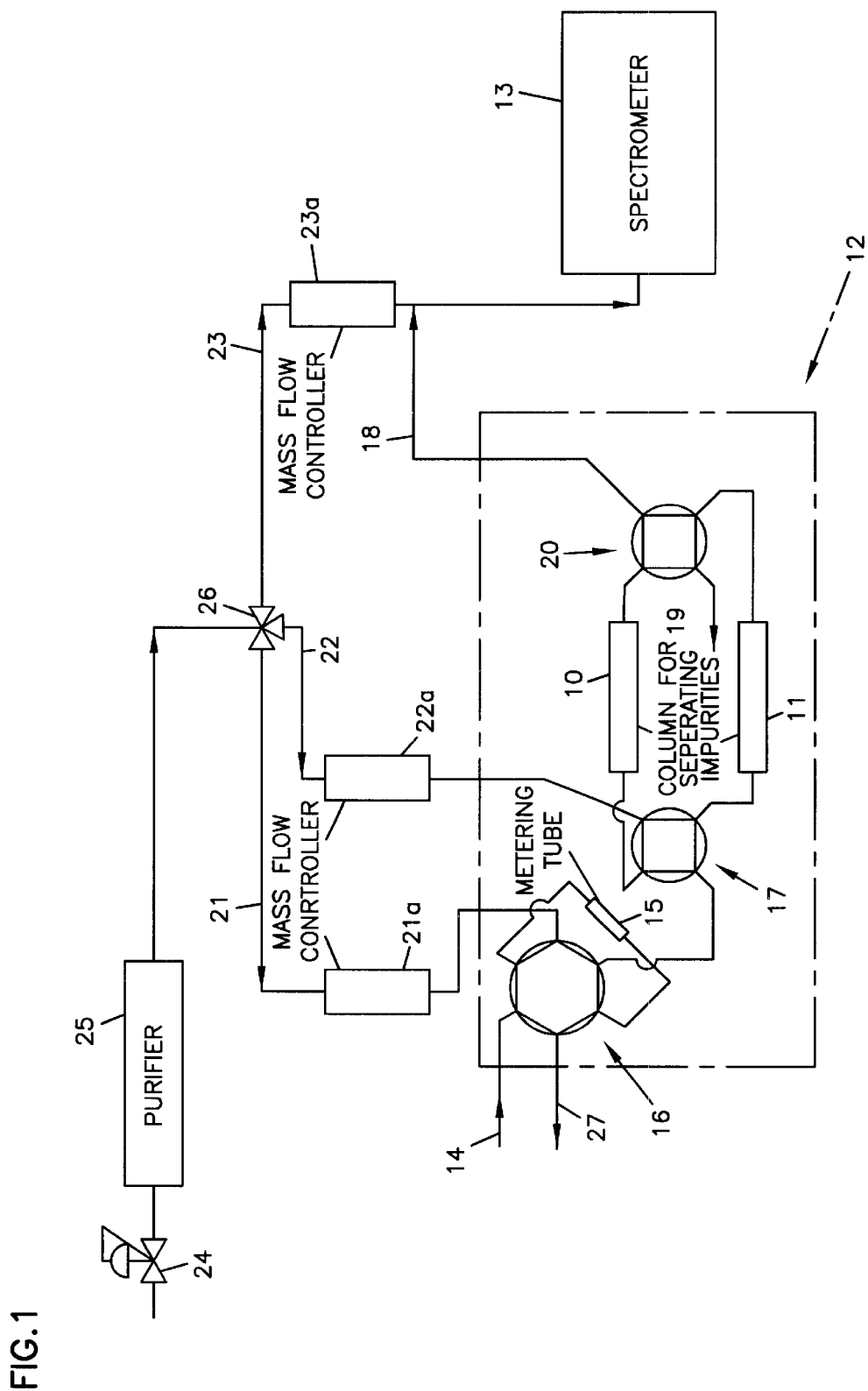
FIG. 1 is a systematic diagram showing an embodiment of an analyzing apparatus for which a method according to the present invention is applicable.

FIG. 1 is a systematic diagram showing an embodiment of an analyzing apparatus for which a method according to the present invention is applicable. In the analyzing apparatus, a gas chromatograph 12 is provided with columns 10, 11 for separating trace impurities in sample gases, and an atmospheric pressure ionization spectrometer 13 as a detector of the gas chromatograph 12 is connected downstream of the gas chromatograph 12.

The above gas chromatograph 12 is provided with a sampling valve 16 comprising a 6-direction gas switch cock provided with a metering tube 15 for metering sample gases supplied from a sample gas introduction passage 14, a sample gas switch valve 17 comprising a 4-direction gas switch cock for switching flow direction of the sample gases metered in the sampling valve 16 into any one of the columns 10, 11, an analyzing gas switch valve 20 comprising a 4-direction gas switch cock for switching gases flowing out from the columns 10, 11 into analyzing passage 18 and exhaust passage 19.

Furthermore, carrier gas supply passages 21, 22, 23 for conveying, purging or diluting the sample gases which are respectively provided with mass flow controllers 21a, 22a, 23a are respectively connected to the sampling valve 16, the sample gas switch valve 17 and the analyzing passage 18.

This analyzing apparatus is formed such that carrier gas supplied via purifier from pressure regulator valve 24 is diverged into the respective carrier gas supply passages 21, 22, 23 through 3-connected 4-direction valve 26, and flow rates of the carrier gas are controlled by the mass flow controller 21a, 22a, 23a to be respectively supplied to the predetermined passages, and trace impurity components in the sample gases are separated in the predetermined columns and then analyzed by the atmospheric pressure ionization spectrometer 13 by operating the sampling valve 16, the sample gas switch valve 17 and the analyzing gas switch valve 20 in a predetermined sequence.

For example, FIG. 1 is showing a case where the gas passages in the respective valves are switched to the thick-lined position and analysis (measurement) is carried out by using the first column 10. At this time, the carrier gas supplied to the sampling valve 16 from the carrier gas supply passage 21 flows into the sample gas switch valve 17 after passing through the metering tube 15, and passes through the first column 10 from the sample gas switch valve 17, and flows into the analyzing passage 18 via the analyzing gas switch valve 20, and flows together with the carrier gas (diluting gas) from the carrier gas supply passage 23 to flow into the atmospheric pressure ionization spectrometer 13. Furthermore, the carrier gas supplied into the sample gas switch valve 17 from the carrier gas supply passage 22 passes through the second column 11, and flows out to the exhaust passage 19 via the analyzing gas switch valve 20.

When the gas passages of the sampling valve 16 are switched into the thin-lined side at this condition, the sample gas from the sample gas introduction passage 14 is made to flow out to the sample gas exhaust passage 27 after passing through the metering tube 15. When the gas passages of the sampling valve 16 are switched again into the thick-lined side, the sample gas in the metering tube 15 is squeezed out by the carrier gas from the carrier gas supply passage 21, and passes through the sample gas switch valve 17. The impurity components in the sample gas are separated by packing material packed in the first column 10, and flow into the atmospheric pressure ionization spectrometer 13 via the analyzing passage 18 from the analyzing gas switch valve 20. Thus, measurement of the impurity components is carried out in the atmospheric pressure ionization spectrometer 13.

In the above analyzing apparatus, in the case of the sample gases having high adsorptivity or reactivity such as oxygen, silane, diborane, phosphine, arsine or the like, measurement of the impurities is carried out by introducing a small amount of the sample gas into the analyzing system plural times with a predetermined time interval. That is to say, when the ion source of the atmospheric pressure ionization spectrometer 13 before starting analysis is in a non-operative state (OFF), the conditioning operation is repeated plural times with an adequate time interval, where the gas passage of the sampling valve 16 is switched to the carrier gas side and the sample gas side while continuing the supply of the carrier gas from at least the carrier gas supply passage 21, and the sample gas in the metering tube 15 is introduced into the analyzing system which reaches the atmospheric pressure ionization spectrometer 13 via the sample gas switch valve 17, the first column 10, the analyzing gas switch valve 20 and the analyzing passage 18.

Thus, by introducing an adequate amount of the sample gas into the analyzing system before starting analysis when the atmospheric pressure ionization spectrometer 13 is in a non-operative state, it is possible to saturate the parts having adsorptivity or reactivity as for the sample gas in the analyzing system with the sample gas, and it is also possible to drastically decrease the effect due to the adsorption or reaction of the sample gas during measurement of the impurities. Furthermore, since the conditioning operation is carried out before starting the analysis operation when the atmospheric pressure ionization spectrometer 13 is in the non-operative state, even though high-concentration oxygen or the Like flows to the ion source, there becomes no such occasion that deterioration of the ion source accelerates.

After the above conditioning is carried out, the ion source of the atmospheric pressure ionization spectrometer 13 is placed in an operative state, and the metered sample gas is introduced into the analyzing system for analysis. Thus, it is possible to directly obtain measurement values having superior reproducibility and to analyze the trace impurities such as hydrogen, nitrogen, methane, carbon monoxide, carbon dioxide or the like with high accuracy. Particularly, in the atmospheric pressure ionization spectrometer 13 capable of measuring the trace impurities of ppb~sub ppb level, since an effect due to the reaction of the sample gas, for example, the background, can be extremely stabilized, it is possible to accurately measure an extremely small amount of impurities.

Introduction amount or introduction interval of the sample gas in this conditioning can be appropriately set according to the conditions of the sample gas, the column, the detector or the like. In general, the introduction amount of the sample gas is enough with the volume of the metering tube 15 of, for example, about several ml, and the introduction interval can be several seconds, however, it can be appropriately selected within a range of two-digit seconds or preferably within a range of several minutes~two-digit minutes practically. For example, when the apparatus starts operating, if several ml of the sample gas is introduced into the analyzing system with several minutes of interval, it is possible to saturate the analyzing system with the sample gas in relatively short time. When the analyzing system is maintained in the saturation state for a long time, for example, several days, it is preferable to introduce the sample gas with the interval less than 2 hours, preferably less than 60 minutes. Furthermore, the introduction number and the introduction amount of the sample gas can be preferably set according to the apparatus scale such as the column shape or the like, or can be preferably confirmed by experiment.

Figure 2:
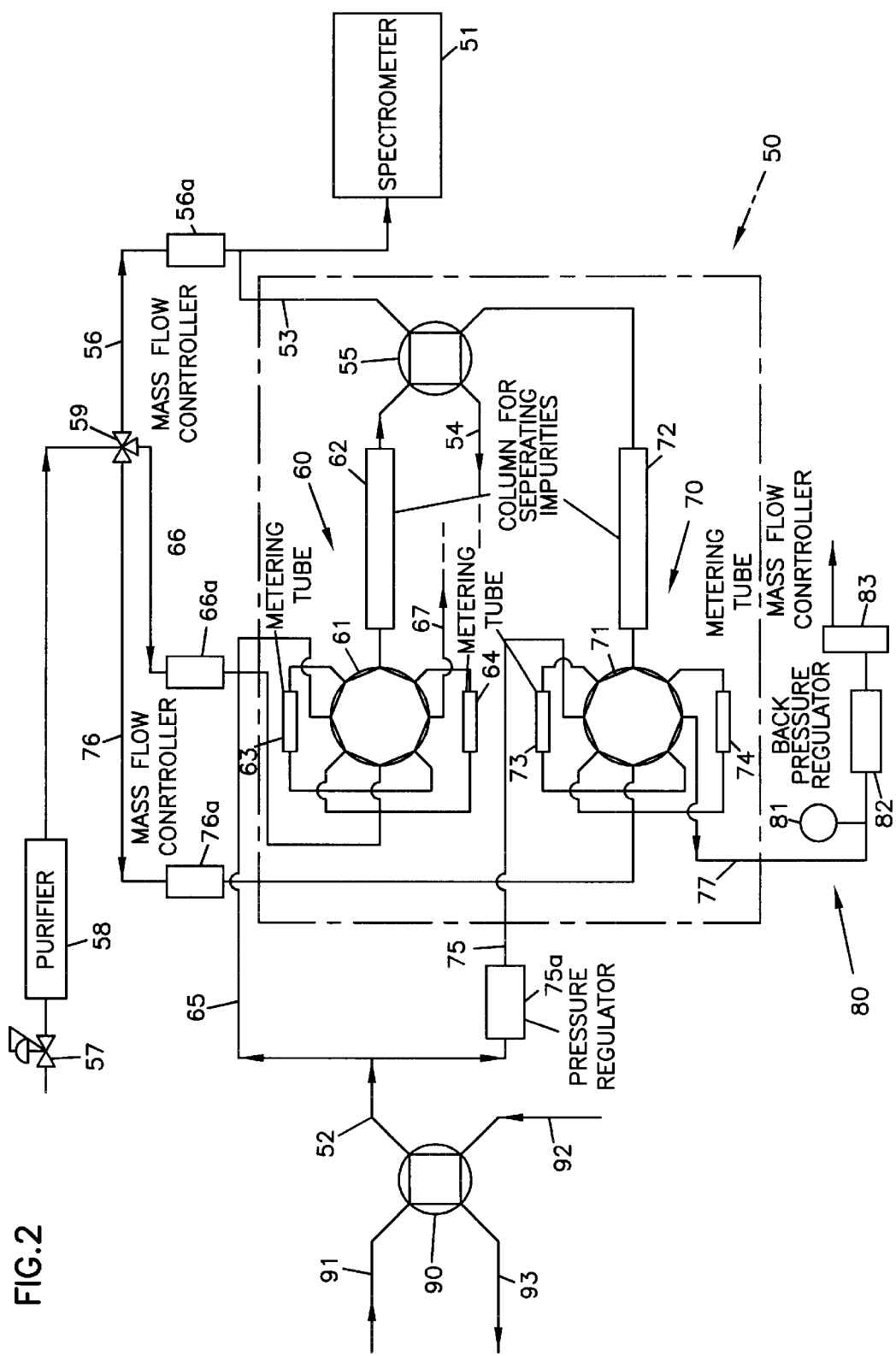
FIG. 2 is a systematic diagram showing another embodiment of the analyzing apparatus according to the present invention.

FIG. 2 is a systematic diagram showing another embodiment of the apparatus according to the present invention, which can execute the above-mentioned method more effectively. In this analyzing apparatus, gas chromatograph 50 and atmospheric pressure ionization spectrometer 51 are combined as in the above embodiment.

The gas chromatograph 50 is provided with first separating passage 60 comprising sampling valve 61 and column 62, second separating passage 70 comprising sampling valve 71 and column 72. Two metering tubes 63, 64, and 73, 74 are switchably provided respectively in the sampling valves 61, 71 by using all-direction gas switch cock. Furthermore, first sample gas introduction passage 65 diverged from the sample gas introduction passage 52, first carrier gas supply passage 66 provided with mass flow controller 66a, and first exhaust passage 67 are connected to the sampling valve 61. Similarly, second sample gas introduction passage 75 diverged from the sample gas introduction passage 52, second carrier gas supply passage 76 provided with mass flow controller 76a, and second exhaust passage 77 are connected to the sampling valve 71 of the second separating passage 70. Furthermore, pressure regulator 75a for maintaining the separating passages 60, 70 with same pressure is provided in the second sample gas introduction passage 75.

Furthermore, analyzing gas switch valve 55 comprising 4-direction gas switch cock for switching the gas flowing out from the columns into the analyzing passage 53 and the exhaust passage 54, is provided in the downstream of the columns 62, 72. The analyzing passage 53 joins with dilution carrier gas supply passage 56 provided with mass flow controller 56a to be connected to the atmospheric pressure ionization spectrometer 51. Furthermore, exhaust system 80 comprising pressure gauge 81, back pressure valve 82 and mass flow meter 83, is provided in the respective exhaust passages 54, 67, 77 (not shown except the exhaust passage 77).

Furthermore, sample gas selection valve 90 comprising 4-direction gas switch cock for switching the sample gases from first introduction passage 91 and second introduction passage 92 into the sample gas introduction passage 52 and sample gas exhaust passage 93, is provided in the sample gas introduction passage 52. Furthermore, carrier gas directed to the respective carrier gas supply passage 56, 66, 76 is diverged at the 3-connected 4-direction valve 59 via purifier 58 from pressure regulator valve 57, to be respectively supplied.

The columns 62, 72 are formed such that the conditions of the packing material to be used such as kind, length, temperature or the like are respectively set according to the kinds of impurities to be analyzed, and the analyzing gas switch valve 55 is switched according to the component to be analyzed, and thus gas separated in any one of the columns 62, 72 can be selectively introduced into the atmospheric pressure ionization spectrometer 51.

Next, a sequence of analyzing impurities in the sample gases by using the above analyzing apparatus will be described. In this regard, a case where first sample gas source continuously carrying out analysis is connected to the first introduction passage 91 of the sample gas introduction passage 52 and second sample gas source carrying out spot analysis is connected to the second introduction passage 92 and respective adequate ones in separating first impurity component and second impurity component are used respectively for the first column 62 and the second column 72, will be described hereinafter.

At first, when the atmospheric pressure ionization spectrometer 51 is in non-operative state, gas passages in the respective valves are positioned as the thick lines of the FIG. 2. and supplies of the respective gases are started. In this condition, the first sample gas from the first introduction passage 91 is diverged into the first sample gas introduction passage 65 and the second sample gas introduction passage 75 via the sample gas introduction passage 52 from the sample gas selection valve 90. is The sample gas diverged into the first sample gas introduction passage 65 passes through the metering tube 63 in the sampling valve 61 and then, is exhausted into the first exhaust passage 67. Furthermore, the sample gas diverged into the second sample gas introduction passage 75 is pressure-regulated in the pressure regulator 75a and flows into the sampling valve 71 and then, is exhausted into the second exhaust passage 77 after passing through the metering tube 74. Furthermore, the second sample gas from the second introduction passage 92 is exhausted into the sample gas exhaust passage 93 from the sample gas selection valve 90.

On the other hand, the carrier gas from the first carrier gas supply passage 66 flows into the first column 62 after passing through the metering tube 64 in the sampling valve 61, and is introduced into the atmospheric pressure ionization spectrometer 51 via the analyzing passage 53 from the analyzing gas switch valve 55. Furthermore, the carrier gas from the second carrier gas supply passage 76 flows into the second column 72 after passing through the metering tube 73 in the sampling valve 71, and is exhausted into the exhaust passage 54 from the analyzing gas switch valve 55. Furthermore, the predetermined amount of the carrier gas is supplied into the atmospheric pressure ionization spectrometer 51 from the carrier gas supply passage 56.

Then, by switching the sampling valve 61, the sample gas in the metering tube 63 is accompanied by the carrier gas from the first carrier gas supply passage 66 to flow into the first column 62, and is introduced into the atmospheric pressure ionization spectrometer 51 via the analyzing passage 53 from the analyzing gas switch valve 55. Furthermore, by switching the sampling valve 71, the sample gas in the metering tube 74 flows into the second column 72, and is exhausted into the exhaust passage 54 from the analyzing gas switch valve 55. At this time, the first sample gas passes through the metering tube 64 to be exhausted into the first exhaust passage 67, and the second sample gas passes through the metering tube 73 to be exhausted into the second exhaust passage 77.

Furthermore, by switching the respective sampling valve 61, 71 in this state, the sample gas in the metering tube 64 and the sample gas in the metering tube 73 respectively flow into the respective directions of the first column 62 and the second column 72. That is to say, by switching the respective sampling valves 61, 71 with an adequate time interval, the sample gases in the respective metering tubes are introduced into the analyzing system positioned after column.

Thus, after the adequate amount of the sample gas is introduced into the analyzing system comprising the sampling valves 61, 71 and the parts having reactivity or adsorptivity are saturated with the sample gas, analysis and measurement of the impurity component is carried out with the atmospheric pressure ionization spectrometer 51 in an operative state. When analyzing the first impurities by using the first separating passage 60, it is possible to carry out the analysis by switching the sampling valve 61 with the gas passages of the analyzing gas switch valve 55 in the state of thick-lined position as shown in FIG. 2.

While the analysis is carried out by using this first separating passage 60, by continuing switching operation of the sampling valve 71, it is possible to continuously carry out the conditioning or the saturation-state maintaining of the sampling valve 70. Since the sampling valves 61, 71 are provided respectively in the first separating passage 60 and the second separating passage 70 to thereby form independent passages, the switching operation of the sampling valve 71 in the second separating passage 70 does not have an effect on the analyzing operation of the first separating passage 60 and thus, it is possible to stably carry out the analysis of the impurities, which used the first separating passage 60.

For example, in the analyzing apparatus shown in FIG. 1, it is necessary to switch the sample gas switch valve 17 in order to introduce the sample gas for the conditioning into the second column 11 when the analysis is carried out in the first column 10. However, since, instead of the carrier gas flowing via the sampling valve 16 from the carrier gas supply passage 21 until now, the carrier gas from the carrier gas supply passage 22 is made to directly flow to the column 10 by switching the sample gas switch valve 17, the pressure in the analyzing system can be varied in an instant, which has a bad effect on analyzing the impurity component in the atmospheric pressure ionization spectrometers 13.

Therefore, as shown in the present embodiment, by providing the respective sampling valves 61, 71 in the respective separating passages 60, 70 such that the separating passages 60, 70 are independent systems, switching operation of the one sampling valve does not have an effect on the analyzing operation of the other sampling valve and thus, it is possible to carry out stable and high-accurate analysis even though the analyzing operation and the conditioning operation are carried out side by side. Therefore, even when the one column is changed, it is possible to carry out the conditioning in the analyzing system comprising the one column, while the other column carries out analysis as usual, and it is also possible to start analysis using the exchanged column in a short time.

When the analysis of the second impurity component is carried out by using the second separating passage 70, it is preferable to switch the analyzing gas switch valve 55. While the analysis is carried out in the second separating passage 70, it is possible to carry out saturation-state maintaining operation in the first separating passage 60 by adequately switching the sampling valve 61. Furthermore, when the sample gas from the second sample gas source connected to the second introduction passage 92 is analyzed, it is preferable to switch the sample gas selection valve 90. The gas sources connected to the first, second introduction passages 91, 92 are optional. However, for example, it is preferable to connect facilities continuously producing or using the sample gas to the first introduction passage 91, and to connect the sample gas or calibration gas carrying out spot analysis to the second introduction 92, or it is also preferable to connect the calibration gas to the first introduction passage 91 and to connect the sample gas bottle to the second introduction passage 92.

Furthermore, packing material to be packed in the columns is optional, for example, when the sample gas is oxygen, it is possible to use molecular sieve or silica gel-based material or porous polymer beads or the like. Furthermore, in the above embodiment, atmospheric pressure ionization spectrometer particularly appropriate for analyzing trace impurities is exemplified as a detector of the analyzing apparatus. However, gas chromatograph mass spectrometer where the mass spectrometer is made to be a detector is applicable and gas chromatograph using a usual detector is also applicable. Furthermore, switching operation of the respective valves can be manually carried out, and also automatically carried out by motor or cylinder.

Embodiment

Hereinafter, embodiments of the present invention and comparative examples will be described. The construction shown in FIG. 2 was used as the analyzing apparatus.

Measurements of carbon dioxide and hydrogen were carried out by using calibration gas containing respectively 30 ppb of carbon dioxide and hydrogen in high purity oxygen. The column for carbon dioxide where silica gel-based packing material (the product name Uni Bead 1S) was packed in the stainless column having 2 mm of diameter and 1 m of length, and the column for hydrogen where zeolite-based packing material (the product name Molecular Sieve 13X) was packed in the stainless column having 2 mm of diameter and 2 m of length are respectively used. The temperature of the column oven was set at 30°. Furthermore, purified helium gas was used as the carrier gas and was supplied respectively to the carbon dioxide side, the hydrogen side and the atmospheric pressure ionization spectrometer side, with respective flow rates of 112 ml/min, 43 ml/min and 300 ml/min. The volume of the metering tube (containing front and rear tube) was 3 ml.

COMPARATIVE EXAMPLE

Figure 3:
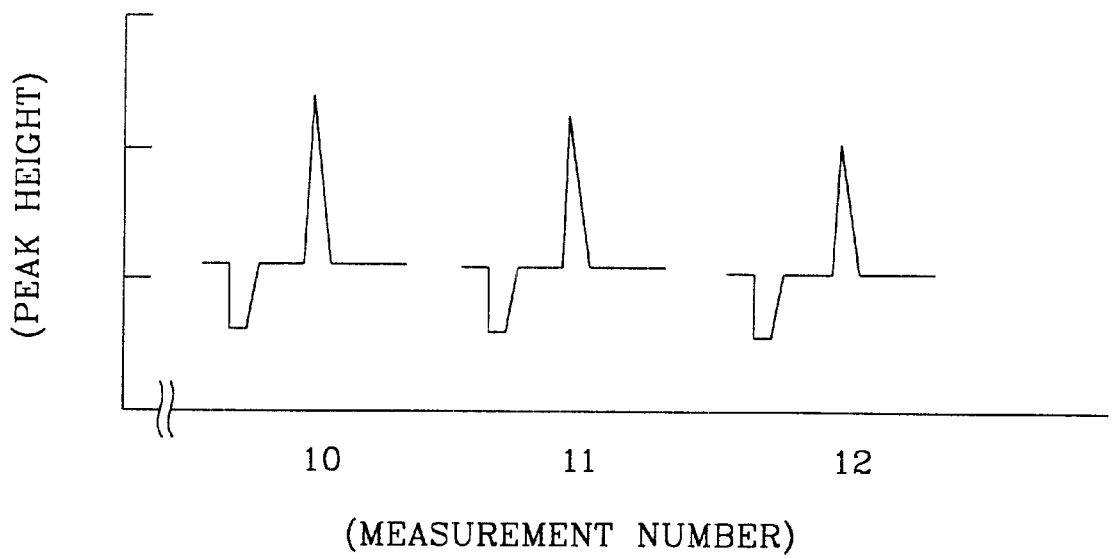
FIG. 3 is a graph showing relationship between measurement time and peak height in comparative example.

According to the conventional method, after the atmospheric pressure ionization spectrometer was made to be in an operative state, the measurement (analysis) of the impurity component in the sample gas (high purity oxygen calibration gas) was started by switching the sampling valve of the measurement side at intervals of 10 minutes. Peak height (peak strength) in measuring hydrogen, was 125 mm at first time, 80 mm at second time, and then varied to 75 mm, 68 mm, 65 mm, 61 mm, 58 mm, 54 mm, 52 mm, and 50 mm at tenth time. Thus, it was impossible to carry out stable measurement after about ten times. Furthermore, as shown in FIG. 3, since peak height or background was varied even after ten times for carbon dioxide, it was impossible to carry out stable measurement.

Consequently, since twelve times of measurements were carried out until the peak height became stable and five times more were carried out after the peak height became stable, about three hours in total were respectively required. Furthermore, the same measurement was carried out three days later, however, more than ten times of measurement operations were similarly required until the peak height became stable. Furthermore, relatively high-concentration oxygen flows into the analyzing part of the atmospheric pressure ionization spectrometer in respective measurement operations, which is considered to have a bad effect on the ion source in operation.

Embodiment

In a preparation step prior to commencement of measurement, when the atmospheric pressure ionization spectrometer was in a non-operative state, flow rates or the like of the respective gases were regulated, and fifteen times of conditioning operations where the sample gas was introduced into the analyzing system by switching the sampling valves at intervals of 10 minutes were repeated. Then, introduction of the sample gas was carried out at intervals of 30 minutes except when in measurement.

Figure 4:
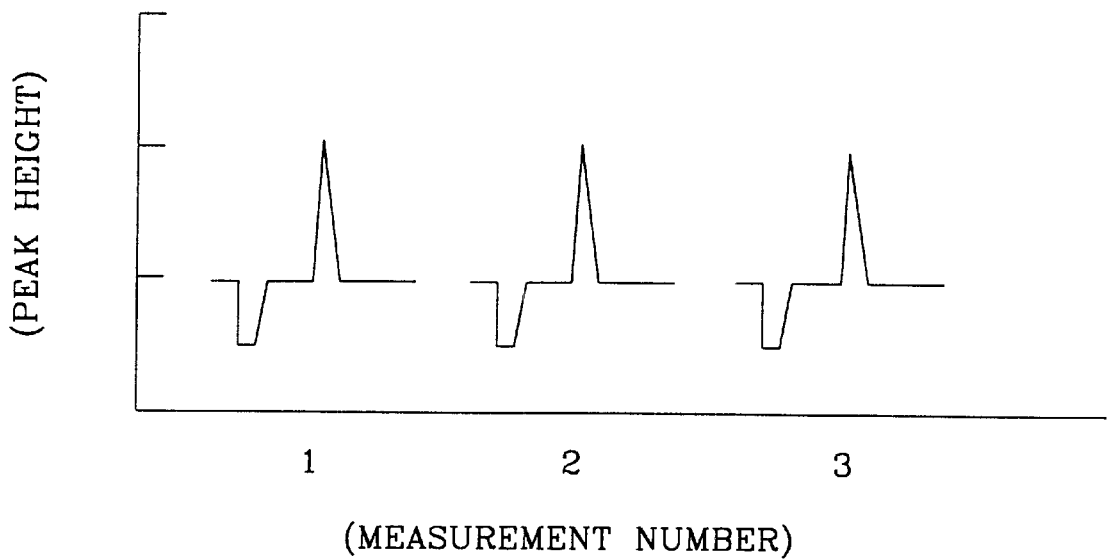
FIG. 4 is a graph showing relationship between measurement time and peak height when carbon dioxide in oxygen is measured according to the embodiment of the present invention.

Three hours later, the atmospheric pressure ionization spectrometer was made to be in an operative state, and measurement of hydrogen followed by that of carbon dioxide was carried out. As a result, stable peak height and background from the first time were obtained for both the measurements. Peak height when carbon dioxide was measured is shown in FIG. 4.

Furthermore, after finishing the above measurement, introduction of 3 ml of the sample gas was continuously carried out at intervals of 1 hour with the atmospheric pressure ionization spectrometer in a non-operative state.

Three days later, when the same measurements were carried out, it was also possible to obtain stable peak height and background, and to carry out accurate measurement with superior reproducibility. Time required in the measurement was about 50 minutes per every five times.

Furthermore, three days later, a cylinder containing high purity oxygen gas (more than 99.99995% of oxygen purity) was connected to the second passage of the sample gas introduction passage, and measurement of carbon dioxide was carried out by switching the sample gas selection valve. Then, peak height and background for five times of measurements were stable, and the analyzed value of carbon dioxide was 2.5 ppb on the average of five times, and coefficient of variation at that time was high-accuracy of 2.1%, which suggested very precise measurement.

As described above, according to the method of the present invention for analyzing trace impurities in gases, it is possible to carry out analysis of impurity component having high adsorptivity or reactivity accurately in a short time. Particularly, when the atmospheric pressure ionization spectrometer is used as a detector, there becomes no occasion to badly affect the ion source. Furthermore, according to the apparatus of the present invention, even when impurity measurement is carried out in one passage, since conditioning or saturation state maintaining operation of the other passage can be continuously carried out without affecting measurement, it is possible to stably and accurately carry out measurement of plural kinds of impurities in a short time.

What is claimed is:

1. A method of conditioning an analyzing system for analyzing impurities in a sample gas, the system comprising chromatographic columns for separating the impurities inside the columns and a detector for detecting said separated impurities wherein the system is conditioned before starting the analysis of said impurities with the detector by saturating the system with the sample gas by releasing predetermined amounts of the sample gas in the system a plurality of times at predetermined time intervals while the detector is in a non-operative state.

2. An apparatus for carrying out the method of claims 3, including an analyzing system comprising chromatographic columns for separating impurities in a sample gas and a detector for analyzing said separated impurities, said apparatus further comprising;

a sample gas introducing passage which diverges into a plurality of passages, each passage having a column and a sampling valve for metering and Supplying said sample gas into the column, and a switch valve for switching gas flowing out from any one of said columns into an analyzing passage for supplying said gas into said detector, and switching gas flowing out from another of said columns into an exhaust passage for exhausting said gas outside of the analyzing system wherein said switch valve is provided downstream of said columns.

\* \* \* \* \*